(12) United States Patent
Bosch et al.

(10) Patent No.: US 7,435,855 B2
(45) Date of Patent: Oct. 14, 2008

(54) PROCESS FOR THE CONTINUOUS SYNTHESIS OF METHYLAMINES

(75) Inventors: Marco Bosch, Mannheim (DE); Jan Kurt Eberhardt, Mannheim (DE); Roderich Röttger, Mannheim (DE); Thomas Krug, Worms (DE); Johann-Peter Melder, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 109 days.

(21) Appl. No.: 11/629,801

(22) PCT Filed: Jun. 16, 2005

(86) PCT No.: PCT/EP2005/006480

§ 371 (c)(1),
(2), (4) Date: Dec. 18, 2006

(87) PCT Pub. No.: WO2005/123658

PCT Pub. Date: Dec. 29, 2005

(65) Prior Publication Data

US 2008/0033212 A1    Feb. 7, 2008

(30) Foreign Application Priority Data

Jun. 18, 2004   (DE) ................ 10 2004 029 544
Jun. 9, 2005    (DE) ................ 10 2005 026 515

(51) Int. Cl.
   C07C 209/14     (2006.01)
(52) U.S. Cl. .................. 564/479; 564/474; 564/480
(58) Field of Classification Search .............. None
   See application file for complete search history.

(56) References Cited

U.S. PATENT DOCUMENTS

| | | | |
|---|---|---|---|
| 4,485,261 A | 11/1984 | Ashina et al. | |
| 4,683,334 A | 7/1987 | Bergna et al. | |
| 4,732,918 A | 3/1988 | Lohmueller et al. | |
| 5,137,854 A | 8/1992 | Segawa et al. | |
| 6,077,984 A | 6/2000 | Drake et al. | |
| 6,380,119 B1 | 4/2002 | Grosch et al. | |
| 2001/0002383 A1 | 5/2001 | Hidaka et al. | |
| 2006/0079718 A1 | 4/2006 | Bosch et al. | |
| 2006/0116517 A1 | 6/2006 | Bosch et al. | |

FOREIGN PATENT DOCUMENTS

| | | |
|---|---|---|
| CN | 1095645 | 11/1994 |
| DE | 125533 | 4/1977 |
| DE | 103 56 184 A1 | 7/2005 |
| EP | 0 118 193 | 9/1984 |
| EP | 0 125 616 | 11/1984 |
| EP | 0 130 407 | 1/1985 |
| EP | 0 534 195 | 3/1993 |
| EP | 0 593 086 A1 | 4/1994 |
| EP | 0 632 012 A2 | 1/1995 |
| EP | 0 967 011 A2 | 12/1999 |
| JP | 61-254256 | 11/1986 |
| JP | 3-262540 | 11/1991 |
| JP | 08 157 428 | 6/1996 |
| JP | 2000-005604 | 1/2000 |
| KR | 2002-0047532 | 6/2002 |
| WO | 99/02483 | 1/1999 |
| WO | WO-01/23089 A1 | 4/2001 |
| WO | WO-03/092887 A1 | 11/2003 |
| WO | 2004/002937 | 1/2004 |

OTHER PUBLICATIONS

Ullmann's Encyclopedia of Industrial Chemistry, vol. A 24, pp. 21-56, (1993).

K. Segawa et al. "Shape-Selective Reactions for Methylamine Synthesis from Methanol and Ammonia". *Stud. Surf. Sci. Catal.*, 75 (1993), 1273-1283.

K. Segawa et al. "Highly Selective Methylamine Synthesis over Modified Mordenite Catalysts". *Journal of Catalysis* 131, 482-490, 1991.

Shokubai, vol. 29, No. 4, 322-326, 1987.

Niwa et al. "Modification of H-Mordenite by a Vapour-phase Deposition Method". *J. Chem. Soc., Chem. Commun.*, 819-820, 1982.

Niwa et al., "Fine Control of the Pore-opening Size of the Zeolite Mordenite by Chemical Vapour Deposition of Silicon Alkoxide". *J. Chem. Soc., Faraday Trans.* 1, 80, 3135-3145, 1984.

J.F. Lepage et al., "Chapter 5: The Preparation of Catalysts". *Applied Heterogeneous Catalysis—Design, Manufacture, Use of Solid Catalysts*, 75-123, 1987.

C. N. Satterfield, "Chapter 4: Cataysr Preparation and Manufacture". *Heterogeneous Catalysis in Industrial Practice*, 87-130, 1991.

E.B.M. Doesburg, "Chapter 8: Preparation of Catalyst Supports and Zeolites". *Studies in Surface Science and Catalysis*, 309-332, 1993.

A. B. Stiles, "Chapter: 1 Getting the Catalyst and the Supported Together" and "Chapter 3: Supports Other then Alumina". Catalyst Supports and Supported Catalysts: Theoretical and Applied Concepts, 1-9 and 57-85, 1987.

*Primary Examiner*—Brian J Davis
(74) *Attorney, Agent, or Firm*—Connolly Bove Lodge & Hutz LLP

(57) ABSTRACT

Process for the continuous synthesis of methylamines by reaction of methanol and/or dimethyl ether with ammonia in the presence of a heterogeneous catalyst, wherein the catalyst used is a shaped body which comprises a microporous material and at least one organosilicon compound as binder and can be produced by a process comprising the steps (I) preparation of a mixture comprising the microporous material, the binder, a pasting agent and a solvent, (II) mixing and densification of the mixture, (III) shaping of the densified mixture to give a shaped body, (IV) drying of the shaped body and (V) calcination of the dried shaped body.

28 Claims, No Drawings

PROCESS FOR THE CONTINUOUS SYNTHESIS OF METHYLAMINES

CROSS REFERENCE TO RELATED APPLICATIONS

This application is a National Stage entry under 35 U.S.C. § 371 of PCT/EP2005/006480 filed on Jun. 16, 2005, which claims priority to German Application Nos. 10 2004 029 544.1, filed on Jun. 18, 2004 and 10 2005 026 515.4, filed on Jun. 9, 2005. The entire contents of each of the above-applications are incorporated herein by reference.

The present invention relates to a process for the continuous synthesis of methylamines by reaction of methanol and/or dimethyl ether with ammonia in the presence of a heterogeneous catalyst, wherein the catalyst used is a shaped body comprising a microporous material and at least one binder.

Monomethylamine (MMA) is an intermediate which is used in the synthesis of pharmaceuticals (e.g. theophyllin), pesticides (carbaryl, metham sodium, carbofuran), surfactants, photographic developers, explosives and solvents such as N-methyl-2-pyrrolidone (NMP).

Dimethylamine (DMA) is likewise a synthetic intermediate. Examples of products based on dimethylamine are fungicides and vulcanization accelerators (zinc bisdimethyldithiocarbamate) (ziram), tetramethylthioperoxydicarboxamide (TMTD), tetramethylthiocarboxamide (MTMT), the propellant 1,1-dimethylhydrazine, various pharmaceuticals, monomers such as dimethylaminoethyl methacrylate, solvents (N,N-dimethylformamide, N,N-dimethylacetamide), catalysts [e.g. 2,4,6-bis-[(dimethylamino)methyl]phenol (DMP 30)], the insecticide dimefax, surfactants and ion exchange resins.

Trimethylamine (TMA) is used in the production of choline salts, cationic starches, disinfectants, flotation agents, sweeteners and ion exchange resins.

The classical synthesis of monomethylamine (MMA), dimethylamine (DMA) and trimethylamine (TMA) is carried out from ammonia and methanol in the gas phase over an amorphous non-shape-selective silica-alumina (mixed forms of aluminum oxide and silicon oxide) at pressure of from 10 to 50 bar. When relatively high temperatures (350 to 475° C.) are employed, thermodynamic equilibrium is established or is approximately reached over these heterogeneous catalysts when the residence time in the reactor is sufficient at the given pressure and the given feed temperature. A characteristic of these "equilibrium catalysts" is a proportion of trimethylamine in the output from the reactor, based on the sum of monomethylamine, dimethylamine and trimethylamine, of from 35 to 60% by weight. The product distribution is dependent on the temperature and on the N/C ratio. The proportion of trimethylamine in the product mixture can be reduced when a relatively high excess of ammonia (greater N/C ratio) is comprised in the reaction mixture. If the proportion of monomethylamine and/or dimethylamine in the desired product mixture taken off after known work-up is greater than that corresponding to the output from the reactor, both the excess trimethylamine and the unreacted ammonia have to be recirculated to the reactor, forming large circulations of ammonia and trimethylamine.

The worldwide consumption of trimethylamine is from 10 to 20% by weight of the total amount of methylamines. It is desirable to increase the proportion of DMA and MMA without recirculation of the reaction mixture. This can be achieved by the use of shape-selective catalysts at temperatures of from 250 to 400° C. A product mixture consisting predominantly of dimethylamine and monomethylamine and comprising only little trimethylamine is obtained.

The shape-selective properties are obtained when the pore diameter of the molecular sieve is smaller than the kinetic diameter of trimethylamine of about 6.1 Å (Stud. Surf. Sci. Catal. 1993, 75, 1273-1283). Preference is given to using molecular sieves having a pore diameter of less than 5.5 Å, particularly preferably less than 5.0 Å.

Molecular sieves having pore diameters of 6.1 Å and above can be converted by means of chemical modifications into shape-selective materials. The modifications result in reduction of the effective pore diameter to less than 5.5 Å, preferably less than 5.0 Å. The modifications comprise partial ion exchange with alkali metal, alkaline earth metal, transition metal and/or lanthanide ions, treatment of the molecular sieve with silicon- and/or phosphorus-comprising substances and/or treatment of the molecular sieve with water vapor.

Particular mention may be made of the treatment of molecular sieves and in particular zeolites with silicon-comprising compounds in the gas phase.

In this gas-phase method, preference is given to reacting mordenite catalysts with silicon compounds such as $SiCl_4$ (JP 262540/1991; J. Catal. 1991, 131, 482; U.S. Pat. No. 5,137, 854) and $Si(OMe)_4$ or $Si(OEt)_4$ (Shokubai, 1987, 29, 322, J. Chem. Soc., Chem. Commun. 1982, 819). Other examples encompassing catalysts based on chabazite, erionite, ZK-5 and Rho and their treatment with silicon-, aluminum-, boron- and/or phosphorus-comprising compounds are described in JP 254256/1986 and U.S. Pat. No. 4,683,334.

The silylation of mordenite catalysts by means of tetraalkoxysilanes in the liquid phase is described in EP-A-593 086.

It is likewise known that, after the silylation, the treated zeolite is subjected to a heat treatment (=calcination step) (J. Chem. Soc., Faraday Trans. 1984, 180, 3135; EP-A-593 086).

Both liquid-phase and gas-phase silylation have the disadvantage that the products formed in the reaction (HCl in the case of $SiCl_4$ or ROH in the case of $Si(OR)_4$) have to be separated from the zeolite powder.

In the case of silylation using $SiCl_4$, industrial use is made more difficult by the corrosive properties of the HCl formed.

After the treatment with $SiCl_4$, one or more step(s) is/are necessary to produce an $SiO_2$ layer. In the case of the silylation of the zeolite powder by means of tetraalkoxysilanes $Si(OR)_4$ in the liquid phase, not only the elimination product ROH formed but also the solvent (usually $C_{1-6}$-alcohols, $C_5$-$C_8$-(cyclo)alkanes and/or toluene) have to be removed and the powder subsequently has to be dried before it can be used in the shaping step.

Additional process steps are thus necessary for both silylation methods in order to produce a silylated catalyst. These additional process steps and/or the products formed in the silylation can make industrial implementation of such methods uneconomical from a cost point of view and/or for practical reasons.

The use of colloidal silica as $SiO_2$ binder for producing shaped catalyst bodies is described in "Catalyst Support and Supportes Catalysts" (A. B. Stiles), 1987, Chapter 1, on pages 1 to 9 and in Chapter 3 on pages 57 to 62, in "Applied Heterogeneous Catalysis—Design, Manufacture, Use Of Solid Catalysts" (J.-F. Lepage, J. Cosyns, P. Courty, E. B. Miller), 1987, Chapter 5, on pages 75 to 123, in "Heterogeneous Catalysis In Industrial Practice" (C. N. Satterfield), 2nd edition, 1991, Chapter 4, on pages 87 to 130 and specifically on page 121, and in "Studies in Surface Science and Catalysis" (E. B. M. Doesburg, J. H. C. Hooff), 1993, Chapter 8 on pages 309 to 332.

The use of colloidal silica and specifically Ludox® AS40 from DuPont as $SiO_2$ binder for the shaping of ZSM-5 powder is described in U.S. Pat. No. 6,077,984.

The earlier German patent application No. 10356184.6 of Dec. 2, 2003 (BASF AG) relates to a particular zeolitic material of the pentasil structure type having an alkali metal and alkaline earth metal content of $\leq 150$ ppm and a specification with regard to spherical primary particles, which is shaped by means of colloidal silica as binder, and its use as catalyst.

Shaped catalyst bodies comprising a ZSM-5 powder and an $SiO_2$ binder and having cutting hardnesses of greater than 1 kg are obtained according to WO-A-01/23089. Colloidal silicas are used as $SiO_2$ binders.

WO-A-03/092887 (DE-A1-102 19 879) (BASF AG) relates to a process for producing a catalyst support, in which zirconium dioxide powder is mixed with a binder and shaped to form shaped bodies, dried and calcined, with the binder being a monomeric, oligomeric or polymeric organosilicon compound. This patent application also provides the resulting catalyst support itself, a catalyst comprising this support and its use as dehydrogenation catalyst.

The shaping of crystalline molecular sieves together with transition metal oxides, sheet silicates and clays and the use of the shaped bodies for the shape-selective preparation of methylamines from methanol and ammonia is described in the patent application JP 2000-005604 (=EP-A-967 011). As crystalline molecular sieves, preference is given to silicoaluminophosphates, mordenites and chabazite. As binders, preference is given to zirconium oxide, yttrium oxide and titanium oxide; the proportion is preferably from 1 to 20% by weight.

CN-A-1 095 645 describes the use of silicon-comprising inorganic substances as inert binder material for the production of shape-selective molecular sieve catalysts which are used for the preparation of methylamines. The weight ratio of binder (based on $SiO_2$ in the finished extrudate) is in the range from 30 to 70% by weight. Gelling agents such as ammonium nitrate, sodium nitrate or potassium nitrate and pore wideners such as surfactants or vegetable starches can be added in the shaping process. The proportion of pore wideners is preferably less than 10% by weight, more preferably from 3 to 7% by weight.

It was an object of the present invention to discover an improved economical process for the preparation of methylamines (MMA, DMA, TMA; in particular DMA). The process should overcome one or more disadvantages of the processes of the prior art. The process should, especially in the reaction of methanol with ammonia, display a high selectivity to dimethylamine (DMA), which is, in particular, higher than in the thermodynamic equilibrium of the methylamines.

We have accordingly found a process for the continuous synthesis of methylamines by reaction of methanol and/or dimethyl ether with ammonia in the presence of a heterogeneous catalyst, wherein the catalyst used is a shaped body which comprises a microporous material and at least one organosilicon compound as binder and can be produced by a process comprising the steps (I) preparation of a mixture comprising the microporous material, the binder, a pasting agent and a solvent,
(II) mixing and densification of the mixture,
(III) shaping of the densified mixture to give a shaped body,
(IV) drying of the shaped body and
(V) calcination of the dried shaped body.

It has surprisingly been found that shaping of a microporous material, in particular a zeolitic material (e.g. a zeolite powder), together with an organosilicon compound (e.g. a silicone) as binder can be carried out successfully and leads to shaped bodies whose mechanical properties (in particular the cutting hardness) is significantly superior to the shaped bodies shaped using colloidal silica, without this improved mechanical stability having an adverse effect on the selectivity and/or activity of the shaped body as catalyst in the preparation of methylamines.

The shaped body used as catalyst in the process of the invention has improved mechanical stability, e.g. measured as cutting hardness (in newton (N)), e.g. a cutting hardness of greater than or equal to 10 N.

In addition, the shaped bodies used as catalysts in the shape-selective synthesis of methylamines make it possible to obtain better conversions and space-time yields, higher selectivities and longer operating lives, e.g. as a result of a reduced tendency for carbon deposits to be formed.

In the process of the invention, the proportion of TMA in the methylamine product mixture is advantageously less than 10% by weight, in particular less than 5% by weight, in each case based on the weight of all three methylamines (MMA, DMA, TMA).

With regard to the shaped catalyst body used in the process of the invention:

The organosilicon compound as binder (step I)

Compounds suitable as organosilicon binder are monomeric, oligomeric or polymeric silanes, alkoxysilanes, acyloxysilanes, oximinosilanes, halosilanes, aminoxysilanes, aminosilanes, amidosilanes, silazanes or silicones as are described, for example, in Ullmann's Encyclopedia of Industrial Chemistry, Vol. A24, on pages 21 to 56, and in Lehrbuch der Anorganischen Chemie (A. F. Holleman, E. Wiberg), 100th edition, Chapter 2.6.5, on pages 786 to 788. In particular, these include the monomeric compounds of the formulae (A) to (F) below:

$$(Hal)_n SiR_{4-x} \quad (A)$$

$$(Hal)_n Si(OR)_{4-x} \quad (B)$$

$$(Hal)_n Si(NR^1R^2)_{4-x} \quad (C)$$

$$R_x Si(OR^1)_{4-x} \quad (D)$$

$$R_x Si(NR^1R^2)_{4-x} \quad (E)$$

$$(RO)_x Si(NR^1R^2)_{4-x} \quad (F)$$

where the radicals Hal are each, independently of one another, halogen (F, Cl, Br or I, in particular Cl), R, $R^1$, $R^2$ are each, independently of one another, H or an optionally substituted alkyl, alkenyl, alkynyl, cycloalkyl, cycloalkenyl, arylalkyl or aryl radical, and x is an integer in the range from 0 to 4.

Among alkyl radicals, preference is given to $C_{1-6}$-alkyl radicals. They can be linear or branched. Preferred examples are methyl, ethyl, n-propyl, n-butyl, sec-butyl and tert-butyl, especially methyl and ethyl.

As aryl radicals, preference is given to $C_{1-6}$-aryl radicals, for example phenyl.

Preferred arylalkyl radicals are $C_{7-20}$-arylalkyl radicals, in particular benzyl.

Preferred alkenyl radicals are $C_{2-6}$-alkenyl radicals, in particular vinyl or allyl.

As alkynyl radicals, preference is given to $C_{2-6}$-alkynyl radicals, for example ethynyl or propargyl.

Among acyl radicals, preference is given to $C_{2-6}$-acyl radicals, in particular acetyl.

Preferred cycloalkyl radicals are $C_{5-8}$-cycloalkyl radicals, in particular cyclopentyl or cyclohexyl.

Preferred cycloalkenyl radicals are $C_{5-8}$-cycloalkenyl radicals, for example 1-cyclopentenyl or 1-cyclohexenyl.

Examples of suitable organosilicon compounds of the formula (A) are $SiCl_4$, $MeSiCl_3$, $Me_2SiCl_2$ and $Me_3SiCl$.

Examples of suitable organosilicon compounds of the formula (B) are $Si(OMe)_4$, $ClSi(OMe)_3$, $Cl_2Si(OMe)_2$, $Cl_3SiOMe$. (Me=methyl)

Examples of suitable organosilicon compounds of the formula (C) are $Si(NMe_2)_4$, $ClSi(NMe_2)_3$, $Cl_2Si(NMe_2)_2$, $Cl_3SiNMe_2$.

Suitable organosilicon compounds of the formula (D) are, for example, $Si(OEt)_4$, $MeSi(OEt)_3$, $Me_2Si(OEt)_2$ and $Me_3Si(OEt)$.

Suitable compounds of the formula (E) are, for example, $Me_3Si(N(Me)COMe)$ and $Me_3Si(N(Me)COCH_2C_6H_5)$.

A suitable compound of the formula (F) is, for example, $(MeO)_3Si(NMe_2)$.

Preference is given to using a cyclic silicone of the formula [—SiO(OR)(R')—]$_x$ or a linear silicone of the formula RO—[SiO(OR)(R')—]$_x$—R, where R and R' are each (independently of one another) $C_{1-6}$-alkyl groups (as defined above), in particular methyl, ethyl, and x is in the range from 2 to 50, in particular in the range from 3 to 20, or a mixture of these silicones as binder.

Very particularly preferred organosilicon binders are methylsilicones, for example the Silres® grades from Wacker, e.g. Silres® MSE100.

To carry out shaping, preference is given to halogen-free organosilicon binders in order to avoid corrosion during the preparation of the shaped bodies or during use of the shaped bodies in the catalytic reaction.

The organosilicon compounds used as binders are preferably liquid under normal conditions or are used as a solution in a preferably nonpolar organic solvent such as hexane, toluene and/or cyclohexane. As a result, the high-surface-area microporous active component is wetted uniformly with the organosilicon compound during mixing. During calcination of the shaped catalyst bodies, the organic radicals of the organosilicon binder burn, forming $SiO_2$ which is very finely dispersed in the shaped body. This results in a high reinforcement of the bonds between the primary particles of the microporous active component and a very good mechanical stability of the resulting shaped catalyst bodies. The combustion of the organic radicals of the organosilicon binder results in additional pores. Owing to the uniform distribution of the organosilicon binder in the shaped body, these pores are likewise very uniformly distributed. As a result, the total porosity of the catalyst support is increased.

The calcination of the shaped bodies in step V preferably results in at least 80% by weight, in particular at least 95% by weight, of the organosilicon compound being converted into finely divided $SiO_2$. The proportion by weight of the resulting finely divided $SiO_2$ in the finished shaped catalyst body is preferably in the range from 5 to 70% by weight, in particular in the range from 10 to 50% by weight, very particularly preferably in the range from 10 to 30% by weight.

The microporous, in particular zeolitic, material (step I)

The microporous material is preferably a molecular sieve having a pore diameter of less than 5 Å. Specific mention may here be made of molecular sieves of the types which can be assigned X-ray-crystallographically to the ABW, ACO, AEI, AEN, AFN, AFT, AFX, ANA, APC, APD, ATN, ATT, ATV, AWO, AWW, BIK, BRE, CAS, CDO, CHA, DDR, DFT, EAB, EDI, ERI, ESV, GIS, GOO, ITE, ITW, JBW, KFI, LEV, LTA, MER, MON, MOR, MTF, PAU, PHI, RHO, RTE, RTH, RUT, SAS, SAT, SAV, THO, TSC, UEI, UFI, VNI, YUG, ZON structures and mixed structures of two or more of the abovementioned structures. The molecular sieve is preferably a crystalline aluminosilicate (=zeolitic material), a crystalline silicoaluminophosphate and/or a crystalline aluminophosphate. Particular preference is given to crystalline aluminosilicates, especially zeolites.

Zeolites are crystalline aluminosilicates which have ordered channel and cage structures and have micropores which are preferably smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolithe Structure Types", Elsevier, 5th edition, Amsterdam 2001.

If desired, it is also possible to use molecular sieves having a pore diameter of greater than 5 Å whose effective pore diameter has been brought to less than 5 Å by means of one or more chemical modifications. Specific mention may here be made of molecular sieves of the types which can be assigned X-ray-crystallographically to the BEA, EUO, FAU, FER, HEU, MEL, MFI, MOR, MWW and OFF structures and mixed structures of two or more of the abovementioned structures. Preferred molecular sieves are a crystalline aluminosilicate (=zeolitic material), a crystalline silicoaluminophosphate and/or a crystalline aluminophosphate. Particular preference is given to crystalline aluminosilicates, especially zeolites.

A general description of the chemical modifications is given in Chapter 3 and especially in Chapters 3.1, 3.3 and 3.5 of "Catalysis and Zeolites; Fundamentals and Applications" (Springer Verlag, Heidelberg, 1999, pp. 81-179). The modifications comprise the partial exchange of the molecular sieve with alkali metal, alkaline earth metal, transition metal and/or lanthanide ions using a method analogous to that described in EP-A-0125 616, treatment of the molecular sieve with boron- and aluminum-comprising compounds using a method analogous to that described in WO-A-99/02483, with silicon-comprising compounds using methods analogous to those described in JP-B2-300 1162, EP-A-593 086 and KR 2002/0047532 or phosphorus-comprising compounds using methods analogous to those described in WO-A-99/02483 and WO-A1-2004/002937, and treatment of the molecular sieve with water (vapor) using a method analogous to that described in EP-A-0130 407. The modifications can be repeated a number of times and be combined with one another.

Among the molecular sieves mentioned above, preference is given to using zeolites of the types which can be assigned X-ray-crystallographically to the CHA, ERI, EUO, FAU, FER, HEU, KFI, LEV, LTA, MEL, MFI, MOR, OFF, PHI, RHO structures and mixed structures of two or more of the abovementioned structures.

A particularly preferred zeolite is mordenite having small-port properties as described in "Catalysis and Zeolites; Fundamentals and Applications" (Springer Verlag, Heidelberg, 1999, pp. 41-42). The small-port mordenite can be prepared synthetically by methods known to those skilled in the art or can be used as natural product.

The microporous material used in (I) is preferably present at least partly in the $H^+$ and/or $NH_4^+$ form. Particular preference is given to at least part of the microporous material used in (I) being in the $H^+$ form, and very particular preference is given to more than 60% (based on the number of Brönsted centers in the zeolite) of it being in the $H^+$ form.

As regards the primary particles of the microporous material used in (I), preference is given to particle sizes of less than 10 μm, particularly preferably less than 5 μm and in particular less than 2 μm. The particle size distribution of the microporous material should be at least 80%, preferably at least 90%, in the range of the preferred particle size.

The geometry of the primary particles is not subject to any restriction. Preference is given to using primary particles having an aspect ratio of greater than 1, preferably greater than 2 and particularly preferably greater than 5. The aspect ratio is defined as the ratio of the length (in μm) to the diameter (in μm) of the primary particles. The primary particles can be present in the powder either as individual particles or as agglomerates consisting of at least two, typically from 2 to 50, primary particles.

The size and geometry of the primary particles as described in the context of the present invention can be determined, for example, by the electron-microscopic methods SEM (scanning electron microscopy) and TEM (transmission electron miscroscopy). The size distribution of the primary particles can be determined, for example, by measurement of the particle size distribution by means of laser light scattering.

The specific surface area of the preferred crystalline zeolitic material, determined in accordance with DIN 66131 (BET), is preferably at least 200 m²/g and particularly preferably at least 300 m²/g. For example, the specific surface area is in the range from 200 to 650 m²/g and in particular in the range from 300 to 550 m²/g.

The pore volume of the preferred crystalline zeolitic material, determined in accordance with DIN 66134 (Langmuir; $p/p_o$=0.9995), is preferably at least 0.5 ml/g, particularly preferably at least 0.6 ml/g and very particularly preferably at least 0.75 ml/g. For example, the pore volume is in the range from 0.5 to 1.5 ml/g, more preferably in the range from 0.6 to 1.4 ml/g and particularly preferably in the range from 0.75 to 1.3 ml/g.

The Solvent (Step 1)

Suitable solvents are, for example, acyclic or cyclic, in particular aliphatic, ethers having from 2 to 12 carbon atoms, e.g. diethyl ether, di-n-propyl ether or its isomers, methyl tert-butyl ether (MTBE), THF, pyran, or lactones such as gamma-butyrolactone, polyethers such as monoglyme, diglyme, etc, aromatic or aliphatic hydrocarbons such as benzene, toluene, xylene, pentane, cyclopentane, hexane and petroleum ether, or mixtures thereof, and in particular also N-methylpyrrolidone (NMP) or water or aqueous organic solvents or diluents of the abovementioned type.

Particular preference is given to using water as solvent, which can also be a diluent.

It is also possible to add either Brönsted acids or Brönsted bases to the water. Suitable Brönsted acids are, for example, hydrochloric acid, sulfuric acid, phosphoric acid, nitric acid or carboxylic acids, dicarboxylic acids or oligocarboxylic or polycarboxylic acids, for example nitrilotriacetic acid, sulfosalicylic acid or ethylenediaminetetraacetic acid.

Suitable Brönsted bases are primary, secondary and tertiary alkylamines, ammonia and also rare earth metal hydroxides, alkali metal hydroxides and alkaline earth metal hydroxides.

The proportion of Brönsted acids or Brönsted bases in the solvent (e.g. water) is preferably in the range from 0.5 to 50% by weight, more preferably from 1 to 25% by weight, particularly preferably from 1.5 to 10% by weight.

The addition of the solvent results in the mixture having the correct consistency for further processing in the shaping step. The proportion of solvent is preferably in the range from 0.5 to 80% by weight, more preferably in the range from 1 to 50% by weight, even more preferably in the range from 2 to 40% by weight and particularly preferably in the range from 3 to 30% by weight, in each case based on the total mass of the mixture prepared in step 1.

The Pasting Agent (Step 1)

In the preparation of the mixture in (I), at least one pasting agent (=organic additive) is added.

As additive (=pasting agent), it is possible to use all compounds suitable for this purpose. These are preferably organic, in parrticular hydrophilic polymers such as cellulose, cellulose derivatives, for example methylcellulose, starches, for example potato starch, polyacrylates, polymethacrylates, polyvinyl alcohol, polyvinylpyrrolidone (PVP), polyisobutene (PIB) or polytetrahydrofuran (PTHF).

In particular, it is possible to use compounds which also act as pore formers as pasting agents.

The pasting agent is preferably used as a solid.

In a particularly preferred embodiment of the process of the invention, as described below, at least 90% by weight of the pasting agent is removed by calcination in step V.

The addition of the pasting agent results in the mixture having the correct consistency for further processing in the shaping step. The proportion of pasting agent is preferably in the range from 0.5 to 80% by weight, more preferably in the range from 1 to 50% by weight, even more preferably in the range from 2 to 40% by weight and particularly preferably in the range from 3 to 30% by weight, in each case based on the total mass of the mixture prepared in step 1.

Pore Formers (Optional, Step 1)

The mixture of binder, the microporous, in particular zeolitic material, pasting agent and solvent prepared in I can be admixed with at least one further compound to aid further processing and to form a plastic composition. Preference is here given to, inter alia, pore formers.

In the process of the invention, it is possible to use all compounds which provide a particular pore size, a particular pore size distribution and/or particular pore volumes in the finished shaped body as pore formers.

Pore formers used in the process of the invention are preferably polymers which can be dispersed, suspended and/or emulsified in water or in aqueous solvent mixtures. Preferred polymers are polymeric vinyl compounds such as polyalkylene oxides, e.g. polyethylene oxides, polystyrene, polyacrylates, polymethacrylates, polyolefins, polyamides and polyesters, carbohydrates such as cellulose or cellulose derivatives, for example methylcellulose, or sugars or natural fibers. Further suitable pore formers are pulp or graphite.

Preference is also given to organic acid compounds which can be removed by calcination in step V, as described below. Mention may here be made of carboxylic acids, in particular $C_{1-8}$-carboxylic acids, such as formic acid, oxalic acid and/or citric acid. It is likewise possible to use two or more of these acid compounds.

If pore formers are used in the preparation of the mixture in step I, the content of pore formers in the mixture prepared in (I) is preferably in the range from 0.5 to 80% by weight, preferably in the range from 1 to 50% by weight and particularly preferably in the range from 2 to 30% by weight, in each case based on the amount of microporous, in particular zeolitic material in the mixture prepared in step (I).

Should it be desirable in order to produce the pore size distribution to be achieved, it is also possible to use a mixture of two or more pore formers.

In a particularly preferred embodiment of the process of the invention, as described below, the pore formers are removed to an extent of at least 90% by weight by calcination in step V to give the porous shaped body. In a preferred embodiment of the process of the invention, shaped bodies having pore volumes determined in accordance with DIN 66134 of at least 0.3 ml/g, preferably in the range from 0.4 to 1.0 ml/g and particularly preferably in the range from >0.4 ml/g to 0.8 ml/g.

The specific surface area of the resulting shaped body used in the process of the invention, determined in accordance with DIN 66131, is preferably at least 200 m$^2$/g and in particular at least 250 m$^2$/g.

For example, the specific surface area is in the range from 200 to 550 m$^2$/g and preferably in the range from 250 to 500 m$^2$/g.

Mixing and Densification (Step II)

After preparation of the mixture in (I), the mixture is homogenized, e.g. for a time in the range from 10 to 180 minutes. Particular preference is given to using, inter alia, kneaders, pan mills or extruders for homogenization. On a relatively small scale, the mixture is preferably kneaded. On a larger, industrial scale, preference is given to using a pan mill for homogenization.

The homogenization is preferably carried out at temperatures in the range from about 10° C. to the boiling point of the solvent and at atmospheric pressure or slightly superatmospheric pressure. At least one of the above-described compounds can then be added if appropriate. The mixture obtained is homogenized, preferably kneaded, until an extrudable plastic composition has been formed.

The homogenized mixture is shaped in a subsequent step.

Shaping of the densified mixture to give a shaped body (step III)

To carry out this step, preference is given to methods in which shaping is effected by extrusion in customary extruders, for example to give extrudates having a diameter of preferably from 1 to 10 mm and particularly preferably from 2 to 5 mm. Such extrusion apparatuses are described, for example, in Ullmann's Enzyklopädie der Technischen Chemie, 4th edition, Vol. 2, p. 295 ff., 1972.

Apart from the use of a screw extruder, preference is likewise given to using a ram extruder for shaping.

However, shaping can in principle be carried out using all known and/or suitable kneading and shaping apparatuses and processes. These include, inter alia:
(i) briquetting, i.e. mechanical pressing with or without addition of additional binder material;
(ii) pelletization, i.e. compaction by means of circular and/or rotating movements;
(iii) sintering, i.e. the material to be shaped is subjected to a thermal treatment.

For example, the shaping method can be selected from the following group, with combinations of at least two of these methods being explicitly included: briquetting by means of punch pressing, roller pressing, annular roller pressing, briquetting without binders; pelletization, fusion, spinning techniques, deposition, foaming, spray drying; firing in a shaft furnace, convection furnace, moving bed furnace, rotary tube furnace, pan milling.

Compaction can take place at ambient pressure or under an increased pressure compared to ambient pressure, for example in a pressure range from 1 bar to a number of hundred bar. Furthermore, compaction can take place at ambient temperature or at an increased temperature compared to ambient temperature, for example in a temperature range from 20 to 300° C. If drying and/or firing are/is constituent(s) of the shaping step, temperatures up to 1500° C. are conceivable. Finally, compaction can take place in the ambient atmosphere or in a controlled atmosphere. Controlled atmospheres are, for example, protective gas atmospheres, reducing atmospheres and/or oxidizing atmospheres.

The shape of the shaped bodies produced according to the invention can be chosen freely. In particular, spheres, oval shapes, cylinders or pellets are possible, inter alia.

For the purposes of the present invention, shaping is particularly preferably carried out by extrusion of the mixture obtained in step II, more preferably to give extrudates which are essentially cylindrical rods having a diameter in the range from 0.5 to 20 mm, preferably in the range from 1 to 10 mm.

The length:diameter ratio of the extrudates is advantageously at least 0.7, in particular at least 1, preferably in the range from >1 to 20, particularly preferably in the range from 2 to 10.

Drying of the Shaped Body (Step IV)

The step (III) is, for the purposes of the present invention, preferably followed by at least one drying step. This at least one drying step is carried out at temperatures in the range of preferably from 80 to 160° C., in particular from 90 to 145° C. and particularly preferably from 100 to 130° C., with the drying time preferably being 6 hours or more, for example in the range from 6 to 24 hours. However, depending on the moisture content of the material to be dried, shorter drying times such as about 1, 2, 3, 4 or 5 hours are also possible.

Before and/or after the drying step, the preferred extrudate can, for example, be comminuted. Here, granular or crushed material having a particle size in the range from 0.1 to 5 mm, in particular from 0.5 to 2 mm, is preferably obtained.

Calcination of the Shaped Body (Step V)

Step (IV) is followed by at least one calcination step. Calcination is carried out at temperatures in the range of preferably from 350 to 750° C. and in particular from 450 to 700° C.

Calcination can be carried out under any suitable gas atmosphere, with air and/or lean air being preferred.

The calcination in (V) can also be carried out in the presence of hydrogen, nitrogen, helium, argon and/or steam or mixtures thereof.

Furthermore, the calcination is preferably carried out in a muffle furnace, a rotary tube furnace and/or a tunnel kiln, with the calcination time preferably being 1 hour or more, for example in the range from 1 to 24 hours or in the range from 3 to 12 hours. Accordingly, it is possible for the purposes of the process of the invention for, for example, the shaped body to be calcined once, twice or more often for a time of in each case at least 1 hour, for example in each case in the range from 3 to 12 hours, with the temperatures during the calcination step being able to remain the same or be changed continuously or discontinuously. If two or more calcination steps are employed, the calcination temperatures in the individual steps can be identical or different.

After the calcination step, the calcined material can, for example, be comminuted. Here, a granular or crushed material having a particle size in the range from 0.1 to 5 mm, in particular from 0.5 to 2 mm, is preferably obtained.

The shaped bodies obtained have hardnesses which are preferably in the range from 2 to 150 N (newton), particularly preferably in the range from 5 to 100 N and very particularly preferably at least 10 N, e.g. in the range from 10 to 75 N.

The above-described hardness is, for the purposes of the present invention, determined by means of an apparatus from Zwick, model BZ2.5/TS1S at an initial force of 0.5 N, and initial force advance rate of 10 mm/min. and a subsequent testing speed of 1.6 mm/min. The instrument had a fixed turntable and a freely movable punch with a built-in cutter having a thickness of 0.3 mm. The movable punch with the cutter was connected to a load cell for recording the force and during the measurement moved toward the fixed turntable on which the shaped catalyst body to be tested was located. The test apparatus was controlled by means of a computer which recorded and evaluated the measured results. The values achieved represent the mean of the measurements on at least 10 shaped catalyst bodies.

After calcination (step V), the shaped body can optionally be treated with a concentrated or dilute Brönsted acid or a mixture of two or more Brönsted acids. Suitable acids are, for example, hydrochloric acid, sulfuric acid, phosphoric acid, nitric acid or carboxylic acids, dicarboxylic acids or oligocarboxylic or polycarboxylic acids, for example nitrilotriacetic acid, sulfosalicylic acid or ethylenediaminetetraacetic acid.

This treatment is carried out in the optionally aqueous liquid phase at a preferred temperature in the range from 10 to 120° C. for a preferred time in the range from 0.5 to 12 hours.

This at least one treatment with at least one Brönsted acid is preferably followed by at least one drying step and/or at least one calcination step, each of which is carried out under the above-described conditions.

In a further preferred embodiment of the process of the invention, the catalyst extrudates can be subjected to a treatment with water vapor to improve hardening, after which they are preferably once again dried at least once and/or calcined at least once. For example, the calcined shaped bodies after at least one drying step and at least one subsequent calcination step are subjected to the treatment with water vapor and are subsequently once again dried at least once and/or calcined at least once.

Use of the shaped catalyst bodies in the process for the continuous synthesis of methylamines by reaction of methanol and/or dimethyl ether with ammonia:

The preparation of methylamines over the catalyst used in the process of the invention is carried out by reaction of ammonia and methanol and/or dimethyl ether in the gas phase at elevated pressure and elevated temperature. If desired, water, monomethylamine, dimethylamine and/or trimethylamine can be added to the reaction mixture or be comprised therein.

The space velocity over the catalyst, expressed in kilogram of methanol per kilogram of catalyst per hour, is preferably in the range from 0.1 to 2.0 $h^{-1}$, in particular in the range from 0.2 to 1.5 $h^{-1}$, very particularly preferably in the range from 0.4 to 1.0 $h^{-1}$. The molar N/C ratio based on the sum of the starting materials is preferably in the range from 0.6 to 4.0, in particular from 0.8 to 2.5, very particularly preferably from 1.0 to 2.0.

The reaction is preferably carried out at a temperature in the range from 250 to 450° C., particularly preferably from 280 to 350° C., very particularly preferably from 290 to 330° C.

The absolute pressure in the reaction is preferably in the range from 5 to 50 bar, especially from 10 to 30 bar, in particular from 15 to 25 bar.

The conversion of methanol is preferably 85%, particularly preferably from 90% to 99%, in particular from 90% to 95%.

The selectivity of the reaction to monomethylamine, dimethylamine and trimethylamine is preferably $\geq$ 95%, particularly preferably $\geq$ 98%.

In the process of the invention, the methylamines are preferably obtained in a weight ratio of monomethylamine (MMA):dimethylamine (DMA):trimethylamine (TMA) of <35:>55:$\leq$10, in particular MMA:DMA:TMA=$\leq$35:$\geq$60:$\leq$5.

The reaction is particularly preferably carried out under isothermal conditions, i.e. at a deviation of not more than +/−20° C., preferably +/−15° C., particularly preferably +/−10° C., in particular +/−5° C., very particularly preferably +/−4° C., from the predetermined reaction temperature.

Suitable reactors for this purpose are shell-and-tube reactors or isothermal reactors as are described, for example, in DE-A-34 14 717 (Linde A G, 'Linde reactor'), in EP-A1-534 195 (BASF AG) and in WO-A1-04/048313 (BASF AG) for the synthesis of methylamines, or adiabatic reactors with intermediate cooling.

The output from the reactor can be worked up by methods based on those known to those skilled in the art, e.g. as described in DD-125 533 (VEB Leuna-Werke).

In the process for the preparation of methylamines using the shape-selective catalyst according to the invention, the reactor comprising the catalyst used according to the invention is preferably combined with a reactor comprising an equilibrium catalyst as described in U.S. Pat. No. 4,485,261 and PEP-Review, No. 89-3-4.

To ensure a long operating life of the shape-selective catalyst, the proportion of aldehydes and in particular the proportion of formaldehyde in the feed should preferably be less than 0.15 g per kg of catalyst per hour (cf. EP-A-342 999).

The dimethyl ether (DME), trimethylamine (TMA) and/or monomethylamine (MMA) which may optionally be used are/is, in particular embodiments of the invention, in each case a corresponding recycle stream from the worked up reaction product of the process.

Regeneration of the shaped catalyst bodies after the continuous synthesis of methylamines by reaction of methanol and/or dimethyl ether with ammonia:

In a further embodiment of the process of the invention, the catalyst is regenerated after use regardless of its shape, e.g. after the activity and/or selectivity have/has decreased, by means of a process in which the regeneration is carried out by targeted burning-off (e.g. at a temperature in the range from 350 to 650° C.) of the deposits responsible for deactivation. This is preferably carried out in an inert gas atmosphere which comprises precisely defined amounts of oxygen or oxygen-supplying substances. Such a regeneration process is described, inter alia, in WO-A-98/55228 and in DE-A1-197 23 949 and in particular for catalysts for the preparation of methylamines in JP-08 157 428 and EP-A-0118 193, whose relevant disclosure is hereby fully incorporated by reference into the present patent application.

After regeneration, the activity and/or the selectivity of the catalyst are/is increased compared to the state immediately prior to regeneration.

The zeolite catalyst which has been used according to the invention and is to be regenerated is heated to a temperature in the range from 250° C. to 800° C., preferably from 400° C. to 650° C. and in particular from 425° C. to 500° C., in an atmosphere comprising from 0.1 to about 20 parts by volume of oxygen-supplying substances, particularly preferably from 0.1 to 20 parts by volume of oxygen, either in the reaction apparatus (reactor) or in an external furnace. Heating is preferably carried out at a heating rate of from 0.1° C./min. to 20° C./min., preferably from 0.3° C./min. to 15° C./min. and in particular from 0.5° C./min. to 10° C./min.

During this heating phase, the catalyst is heated to a temperature at which the usually organic deposits present there begin to decompose, while at the same time the temperature is regulated via the oxygen content and thus does not rise to such an extent that damage to the catalyst structure occurs. At high organic loadings on the catalyst to be regenerated, the slow increase in the temperature and the residence at low temperature resulting from setting of the appropriate oxygen content and an appropriate heating power is an essential step for preventing local overheating of the catalyst.

When the temperature of the offgas stream at the outlet from the reactor drops despite increasing amounts of oxygen-supplying substances in the gas stream and/or the concentration of oxygen in the output from the reactor increases to the value at the inlet, the burn-off of the organic deposits is complete. The duration of the treatment is preferably from 1 to 30 hours, more preferably from about 2 to about 20 hours and in particular from about 3 to about 10 hours.

The subsequent cooling of the catalyst which has been regenerated in this manner is preferably not carried out too quickly, since otherwise the mechanical strength of the catalyst can be adversely affected.

It can be necessary to subject the catalyst which has been regenerated by calcination as described above to rinsing with water and/or dilute acids such as hydrochloric acid in order to remove any remaining inorganic loading of the catalyst due to impurities in the starting material (traces of alkali, etc.). Renewed drying and/or renewed calcination of the catalyst can subsequently be carried out.

In a further embodiment of the process of the invention, the at least partially deactivated catalyst is washed with a solvent in the reactor used for the reaction or in an external reactor to remove adhering desired product before the heat treatment in the regeneration procedure. In this case, washing is carried out so that the desired products adhering to the catalyst can in each case be removed therefrom, but the temperature and pressure are not so high that the usually organic deposits are likewise removed. The catalyst is preferably merely rinsed with a suitable solvent. Solvents suitable for this washing procedure are also solvents in which the respective reaction product dissolves readily. The amount of solvent used and the duration of the washing procedure are not critical. The washing procedure can be repeated a number of times and can be carried out at elevated temperature. When $CO_2$ is used as solvent, supercritical pressure is preferred; otherwise, the washing procedure can be carried out under atmospheric pressure or under superatmospheric or supercritical pressure. After the washing procedure is complete, the catalyst is generally dried. Although the drying procedure is generally not critical, the drying temperature should not exceed the burning point of the solvent used for washing to an excessively great extent in order to avoid sudden vaporization of the solvent in the pores, in particular in the micropores, since this, too, can lead to damage to the catalyst.

In a preferred embodiment of the preparative process, the continuous process of the invention for the synthesis of methylamines is carried out so that it does not have to be interrupted during regeneration of the catalyst used according to the invention, so that the throughput of the process is increased. This can be achieved by the use of at least two reactors which are connected in parallel and can be operated alternately.

Catalyst regeneration can be carried out so that at least one of the parallel reactors is taken out of operation from the respective reaction step and the catalyst comprised in this reactor is regenerated, while at least one reactor is always available for reaction of the starting material or starting materials in each step during the course of the continuous process.

EXAMPLES

The BET surface areas ($m^2/g$) and the pore volumes (ml/g) were determined in accordance with the standards DIN 66131 and DIN 66134.

GC Analysis:

The outputs from the reaction were analyzed by means of on-line gas chromatography. The methylamines were separated on a GC column optimized for short-chain amines (Varian CP-Volamine), and a thermal conductivity detector (TCD) was used for detection. The content of unreacted methanol was determined, and the activity of the catalyst was deduced therefrom.

The determination/measurement of the cutting hardness was carried out as described in WO-A-04/108280 (BASF AG):

The cutting hardnesses were measured in an apparatus from Zwick (model: BZ2.5/TS1S; initial force: 0.5 N, initial force speed: 10 mm/Min.; test speed: 1.6 mm/min.) and are the means from in each case 10 measured catalyst extrudates.

In detail, the cutting hardness was carried out as follows (see also further above in the description):

Extrudates were loaded with increasing force by means of a cutter having a thickness of 0.3 mm until the extrudate was parted. The force required for this is the cutting hardness in N (newton). The determination was carried out on a test instrument from Zwick, Ulm, having a fixed turntable and a freely movable punch with a built-in cutter having a thickness of 0.3 mm. The movable punch with the cutter was connected to a load cell for recording the force and during the measurement moved toward the fixed turntable on which the extrudate to be measured was located. The test apparatus was controlled by means of a computer which recorded and evaluated the measured results. 10 straight, if possible crack-free extrudates having a mean length of from 2 to 3 times the diameter were taken from a well-mixed catalyst sample, their cutting hardnesses were determined and subsequently averaged.

Comparative Example 1

150 g of synthetic small-port mordenite (H form, Si/Al=6.0) together with 71 ml of water, 93 g of Ludox® AS40 (=colloidal silica) and 7.5 g of methylcellulose were mixed in a mechanical kneader for 60 minutes. The paste was then shaped in a ram extruder to give 2 mm extrudates. The extrudates were dried at 120° C. for 16 hours and subsequently calcined in a stream of air at 500° C. in a muffle furnace for 5 hours. This gave 164 g of catalyst. The cutting hardness of the extrudates was 2.1 N. The catalyst extrudates were crushed through a 1.6 mm sieve and the fraction between 1.6 and 0.5 mm was collected.

Example 1

The catalyst was produced by a method analogous to comparative example 1 from 105 g of synthetic small-port mordenite (H form, Si/Al=6.0), 73 ml of water, 37 g of Silres® MSE100 (=methylsilicone in toluene) and 5.2 g of methylcellulose. This gave 109 g of catalyst. The cutting hardness of the extrudates was 25 N. The catalyst extrudates were crushed through a 1.6 mm sieve and the fraction between 1.6 and 0.5 mm was collected.

Example 2

The catalyst was produced by a method analogous to comparative example 1 from 150 g of synthetic small-port mordenite (H form, Si/Al=6.0), 52 ml of water, 93 g of Ludox® AS40, 11 g of Silres® MSE100 and 7.5 g of methylcellulose. This gave 164 g of catalyst. The cutting hardness of the extrudates was 5.4 N. The catalyst extrudates were crushed through a 1.6 mm sieve and the fraction between 1.6 and 0.5 mm was collected.

Synthesis Example 1

25 ml of catalyst from comparative example 1 were installed in an electrically heated tube reactor (length: 50 cm, diameter: 12 mm). The catalyst was baked overnight at 320° C. under a stream of nitrogen. $NH_3$ (18.1 g/h) and methanol (18.9 g/h) were then metered in at 20 bar. After a period of operation of 10 hours, the output from the reaction was analyzed by gas chromatography.

The methanol conversion was 99.6%. The ratio of monomethylamine (MMA), dimethylamine (DMA) and trimethylamine (TMA) based on the three methylamines formed was 29:46:25% by weight.

Synthesis Example 2

The experiment was carried out by a method analogous to synthesis example 1, but using the catalyst from example 1. After 10 hours, the methanol conversion was 98.3%, and the ratio of MMA:DMA:TMA was 34:65:1% by weight (based on the three methylamines formed).

After a period of operation of 30 hours, the methanol conversion was 97.5% and the ratio of MMA:DMA:TMA was 34:65:1% by weight (based on the three methylamines formed).

Synthesis Example 3

The experiment was carried out by a method analogous to synthesis example 1, but using the catalyst from example 2. After 10 hours, the methanol conversion was 98.8%, and the ratio of MMA:DMA:TMA was 33:63:4% (based on the three methylamines formed).

After a period of operation of 30 hours, the methanol conversion was 98.4% and the ratio of MMA:DMA:TMA was 33:63:4% by weight (based on the three methylamines formed).

The inveintion claimed is:

1. A process for the continuous synthesis of methylamines by reaction of methanol and/or dimethyl ether with ammonia in the presence of a heterogeneous catalyst,
   wherein the catalyst used is a shaped body which comprises a microporous material and at least one organosilicon compound as binder and can be produced by a process comprising;
   (I) preparation of a mixture comprising the microporous material, the binder, a pasting agent and a solvents;
   (II) mixing and densification of the mixture;
   (III) shaping of the densified mixture to give a shaped body;
   (IV) drying of the shaped body; and
   (V) calcination of the dried shaped body.

2. The process according to claim 1, wherein a silicone is used as binder in the process for producing the shaped catalyst body.

3. The process according to claim 1, wherein a methylsilicone is used as binder in the process for producing the shaped catalyst body.

4. The process according to claim 1, wherein a cyclic silicone of the formula [—SiO(OR)(R')—]$_x$ or a linear silicone of the formula RO-[—SiO(OR)(R')—]$_x$—R, where R and R' are $C_{1-6}$—alkyl groups and x is in the range from 2 to 50, or a mixture of these silicones is used as binder in the process for producing the shaped catalyst body.

5. The process according to claims 1, wherein at least 80% by weight of the organosilicon compound is converted into finely divided $SiO_2$ by the calcination of the shaped bodies in (V) and a proportion by weight of the resulting finely divided $SiO_2$ in the shaped body is in the range from 5 to 70% by weight.

6. The process according to claim 5, wherein the proportion by weight of the resulting finely divided $SiO_2$ in the shaped body is in the range from 10 to 50% by weight.

7. The process according to claim 1, wherein the calcination in (V) is carried out in the presence of air, hydrogen, nitrogen, helium, argon and/or steam or a mixture thereof.

8. The process according to claim 1, wherein the microporous material used in (I) in the process for producing the shaped catalyst body is a crystalline silicalite, a crystalline aluminosilicate, a crystalline silicoaluminophosphate and/or a crystalline aluminophosphate.

9. The process according to claim 8, wherein the crystalline aluminosilicate is a zeolite and has a MOR, CHA, ERI, KFI, RHO, BEA, FAU, OFF, NES, HEU, FER, MFI or MEL.

10. The process according to claim 9, wherein the zeolite is a mordenite having small-port properties.

11. The process according to claim 8, wherein the crystalline aluminosilicate has a specific surface area (in accordance with DIN 66131 (BET)) of at least 200 $m^2$/g and comprises pores having a pore volume of at least 0.5 ml/g (in accordance with DiN 66134 (Langmuir)).

12. The process according to claim 1, wherein the solvent used in (I) in the process for producing the shaped catalyst body is water.

13. The process according to claim 1, wherein the pasting agent used in (I) in the process for producing the shaped catalyst body is cellulose, a cellulose derivative and/or a starch.

14. The process according to claim 1, wherein the mixture used in (I) in the process for producing the shaped catalyst body further comprises at least one pore former.

15. The process according to claim 14, wherein the pore former is a polyalkylene oxide, polyacrylate, pulp and/or graphite.

16. The process according to claim 1, wherein the shaping in (III) in the process for producing the shaped catalyst body is carried out by extrusion.

17. The process according to claim 16, wherein a diameter of extrudates is in the range form 0.5 to 20 mm and the length-to-diameter ratio is in the range from 0.7 to 10.

18. The process according to claim 1, wherein the calcination in (V) in the process for producing the shaped catalyst body is carried out at a temperature in the range from 350 to 750° C. and for a time in the range from 1 to 24 hours.

19. The process according to claim 1, wherein the shaped catalyst body has a cutting hardness of at least 10 N.

20. The process according to claim 1, wherein the shaped catalyst body has a specific surface area (in accordance with DIN 66131 (BET)) of at least 200 $m^2$/g and comprises pores having a pore volume of at least 0.3 ml/g (in accordance with DIN 66134 (Langmuir)).

21. The process according to claim 1, wherein the microporous material in the shaped catalyst body as set forth in claim 1 (I) is present at least partly in the $H^+$ and/or $NH_4^+$ form.

22. The process according claim 1, wherein the reaction comprises a feed stream comprising methanol and/or dimethyl ether and ammonia together with monomethylamine, dimethylamine and/or trimethylamine.

23. The process according to claim 1, wherein the reaction comprises a feed stream having a molar N/C ratio in the range from 0.6 to 4.0.

24. The process according to any claim 1, wherein a reaction temperature is in the range from 250 to 450° C.

25. The process according to claim 1, wherein an absolute pressure is in the range from 5 to 50 bar.

26. The process according to claim 1, wherein a space velocity over the catalyst, expressed in kilograms of methanol per kilogram of catalyst per hour, is in the range from 0.1 to 2.0 $h^{-1}$.

27. The process according to claim 1, wherein a proportion of trimethylamine (TMA) in the product mixture based on the sum of the methylamines is less than 10% by weight.

28. The process according to claim 1, wherein a regeneration of the catalyst used is carried out by targeted burning-off of the deposits responsible for deactivation.

* * * * *